US008936547B2

(12) United States Patent
Shibuya

(10) Patent No.: US 8,936,547 B2
(45) Date of Patent: Jan. 20, 2015

(54) ENDOSCOPE GAS FEED SYSTEM, ENDOSCOPE, AND ENDOSCOPE SYSTEM

(75) Inventor: Hiroshi Shibuya, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 160 days.

(21) Appl. No.: 13/293,477

(22) Filed: Nov. 10, 2011

(65) Prior Publication Data

US 2012/0123209 A1    May 17, 2012

(30) Foreign Application Priority Data

Nov. 12, 2010    (JP) ................ 2010-254132

(51) Int. Cl.
| | |
|---|---|
| *A61B 1/12* | (2006.01) |
| *A61B 1/06* | (2006.01) |
| *A61B 1/00* | (2006.01) |
| *A61B 1/015* | (2006.01) |
| *A61B 1/32* | (2006.01) |
| *A61B 1/273* | (2006.01) |
| *A61B 1/31* | (2006.01) |

(52) U.S. Cl.
CPC ............. *A61B 1/00091* (2013.01); *A61B 1/015* (2013.01); *A61B 1/32* (2013.01); *A61B 1/2736* (2013.01); *A61B 1/31* (2013.01)
USPC ............................ 600/169; 600/156; 600/157

(58) Field of Classification Search
CPC .... A61B 1/015; A61B 1/126; A61B 1/00091; A61B 1/253; A61B 1/127
USPC .......................................... 600/156, 157, 158
See application file for complete search history.

(56) References Cited

U.S. PATENT DOCUMENTS

| | | | | | |
|---|---|---|---|---|---|
| 4,748,970 | A | * | 6/1988 | Nakajima | 600/158 |
| 5,047,010 | A | * | 9/1991 | Ams et al. | 604/26 |
| 6,652,452 | B1 | * | 11/2003 | Seifert et al. | 600/140 |

(Continued)

FOREIGN PATENT DOCUMENTS

| | | |
|---|---|---|
| EP | 1 852 056 A1 | 11/2007 |
| JP | 06-335447 A | 12/1994 |

(Continued)

OTHER PUBLICATIONS

European Search Report dated Feb. 6, 2012.

(Continued)

*Primary Examiner* — Anhtuan T Nguyen
*Assistant Examiner* — Rynae Boler
(74) *Attorney, Agent, or Firm* — McGinn IP Law Group, PLLC

(57) ABSTRACT

An endoscope gas feed system includes a fluid curtain nozzle for blowing a fluid curtain-forming gas toward an observation window provided on a distal end surface of the insertion part of an endoscope, the distal end surface including at least the observation window and an opening for spraying a constant-pressure feed gas, and the fluid curtain nozzle is provided on an opposite side of the opening with respect to the observation window, a gas/water feed nozzle for cleaning the observation window, the gas/water feed nozzle being provided on the distal end surface, a constant-pressure gas feed unit for supplying the constant-pressure feed gas, so as to spray the constant-pressure feed gas from the opening, and a fluid curtain-forming gas feed unit for supplying a gas, so as to blow the fluid curtain-forming gas from the fluid curtain nozzle.

20 Claims, 4 Drawing Sheets

(56) References Cited

U.S. PATENT DOCUMENTS

| | | | |
|---|---|---|---|
| 2001/0025135 A1* | 9/2001 | Naito et al. | 600/156 |
| 2001/0039370 A1 | 11/2001 | Takahashi et al. | |
| 2005/0222491 A1 | 10/2005 | Noda et al. | |
| 2007/0163585 A1 | 7/2007 | Uesugi et al. | |
| 2007/0229954 A1 | 10/2007 | Bral | |
| 2007/0244363 A1 | 10/2007 | Sano et al. | |
| 2007/0255106 A1* | 11/2007 | Kawanishi | 600/159 |
| 2007/0255107 A1 | 11/2007 | Kawanishi | |
| 2009/0054728 A1* | 2/2009 | Trusty | 600/114 |
| 2009/0299336 A1* | 12/2009 | Jay-Robinson | 604/533 |
| 2010/0256448 A1* | 10/2010 | Smith et al. | 600/156 |

FOREIGN PATENT DOCUMENTS

| | | | | |
|---|---|---|---|---|
| JP | 2005-176908 A | | 7/2005 | |
| JP | 2005176908 A | * | 7/2005 | ............... A61B 1/00 |
| JP | 2005-287839 A | | 10/2005 | |
| JP | 2007-296164 A | | 11/2007 | |
| JP | 2009-106360 A | | 5/2009 | |
| WO | WO 2007/080971 A1 | | 7/2007 | |

OTHER PUBLICATIONS

Japanese Office Action dated Oct. 18, 2012.
Notification of Reasons for Rejection (Japan), with partial English translation, dated May 31, 2013.

\* cited by examiner

ENDOSCOPE GAS FEED SYSTEM, ENDOSCOPE, AND ENDOSCOPE SYSTEM

BACKGROUND OF THE INVENTION

1. Field of the Invention

The present invention relates to an endoscope gas feed system, an endoscope and an endoscope system. More particularly, the invention relates to an endoscope gas feed system, an endoscope and an endoscope system in which intraluminal observations and treatments are performed by supplying a constant-pressure gas from a gas feed unit into a lumen of a subject being tested through an opening provided at a distal end portion of a flexible endoscope inserted into the lumen.

2. Description of the Related Art

Conventionally, medical diagnostics using an endoscope has been widely practiced in the field of medicine. In particular, an image pickup element, such as a CCD, is built into a distal end portion of an endoscope to be inserted into a body cavity to take an image of the interior of the body cavity, and signal processing is performed using a processor unit to display the image on a monitor, so that a doctor observes and uses this image for diagnosis or inserts a treatment instrument from a treatment instrument insertion channel to perform treatments, such as sample collection and polyp removal.

In particular, when an insertion part of a flexible endoscope having flexibility is inserted into a lumen, such as a stomach or a large intestine, to perform intraluminal diagnoses or treatments, a treatment instrument is inserted into a lumen through a forceps channel (treatment instrument channel) of the flexible endoscope to perform curative treatments therein.

At this time, a constant-pressure feed gas, such as a carbon dioxide gas, is supplied into the lumen to expand the lumen, in order to secure the visual field of the flexible endoscope and a space for operating treatment instruments.

For example, Japanese Patent Application Laid-Open No. 2009-106360 discloses a laparoscopic surgery system in which a plurality of trocars is punctured into the abdomen of a patient, a rigid endoscope is inserted into an abdominal cavity from one of the trocars, and a pneumoperitoneum gas supplied from a pneumoperitoneum unit is introduced into the abdominal cavity through another trocar. In addition, a flexible endoscope is inserted into a lumen, such as a large intestine and, thus, these two endoscopes are used in the system. In this system, a carbon dioxide gas is introduced as a pneumoperitoneum gas from the pneumoperitoneum unit into the abdominal cavity through the another trocar in a state of being regulated to a predetermined pressure, so that the carbon dioxide gas is supplied into the lumen through the treatment instrument channel of the flexible endoscope.

In addition, Japanese Patent Application Laid-Open No. 2007-296164, for example, discloses a system in which a gas for securing the visual field of an observation window and a pneumoperitoneum gas are sprayed from a spray nozzle provided at the leading rigid portion of the insertion part of an endoscope. Particularly in order to reduce an operator's frequency of operating a gas/water feed valve used to clean the observation window so as to remove contaminants attached thereto, a carbon dioxide gas is automatically sprayed from the spray nozzle along surfaces of the observation window, thereby forming a fluid curtain thereon.

Yet additionally, Japanese Patent Application Laid-Open No. 2005-176908, for example, discloses a system equipped with a pneumoperitoneum gas circulation mechanism in which distal end openings of the starting end-side and terminal end-side flow paths of a fluid curtain are disposed in upper and lower positions across an observation window disposed on the distal end surface of an endoscope, so as to be substantially in alignment with the observation window, thereby supplying and exhausting a pneumoperitoneum gas within an abdominal cavity to circulate the gas.

However, if a constant-pressure gas supply is provided through an opening of the treatment instrument channel, such as a forceps port, formed on the distal end portion of the flexible endoscope, as in the system described in, for example, Japanese Patent Application Laid-Open No. 2009-106360 mentioned above, bubbles are generated near a gas spray port by bodily fluids and water attached to the distal end surface of the endoscope. Thus, the system has had the problem that those bubbles attach to an observation window (image pickup unit) formed on the distal end surface of the endoscope and interrupt the visual field of the observation window.

In the systems described in Japanese Patent Application Laid-Open Nos. 2007-296164 and 2005-176908, a fluid curtain is formed on the distal end surface in which the observation window is formed to remove contaminants attached thereto. However, none of these systems are configured to provide a constant-pressure supply of a pneumoperitoneum gas from the distal end surface of the flexible endoscope. The endoscope used is a rigid endoscope and the pneumoperitoneum gas is supplied into an abdominal cavity through a trocar. In particular, the system described in Japanese Patent Application Laid-Open No. 2005-176908 removes contaminants splashed on the observation window by the flow of a circulating pneumoperitoneum gas formed on a surface of the observation window. In addition, the system suppresses variations in a gas pressure within the abdominal cavity by circulating the gas while achieving a pressure balance between discharge at the distal end opening of the starting end-side flow path of the fluid curtain and suction at the distal end opening of the terminal end-side flow path of the fluid curtain.

As described above, the systems described in Japanese Patent Application Laid-Open Nos. 2007-296164 and 2005-176908 are not configured to provide a constant-pressure supply of a pneumoperitoneum gas from the distal end surface. Thus, no consideration has been given to the problem that the visual field of the observation window is interrupted by bubbles generated at the distal end surface.

SUMMARY OF THE INVENTION

The present invention has been accomplished in view of such circumstances as described above. Accordingly, an object of the present invention is to provide an endoscope gas feed system, an endoscope and an endoscope system in which the visual field of an observation window is prevented from being interrupted by bubbles generated near a gas spray port when a constant-pressure gas supply is provided through an opening formed on the distal end surface of a flexible endoscope, thereby securing the field of vision.

In order to achieve the above-described object, a first aspect of the present invention provides an endoscope gas feed system comprising: a fluid curtain nozzle for blowing a fluid curtain-forming gas toward an observation window provided on a distal end surface of the insertion part of an endoscope including at least the observation window and an opening for spraying a constant-pressure feed gas and on an opposite side of the opening with respect to the observation window; a constant-pressure gas feed unit for supplying the constant-pressure feed gas, so as to spray the constant-pressure feed gas from the opening; and a fluid curtain-forming gas feed unit for supplying a gas, so as to blow the fluid curtain-forming gas from the fluid curtain nozzle.

Consequently, even if bubbles are generated by a gas sprayed from the opening for spraying the constant-pressure feed gas, the bubbles are moved to a side opposite to the observation window by a fluid curtain. Accordingly, when a constant-pressure gas supply is provided through the opening formed on the distal end surface of the endoscope, the visual field of the observation window can be prevented from being interrupted by bubbles generated near a gas spray port, thereby securing the visual field of the observation window.

In addition, as shown in a second aspect of the present invention, the endoscope gas feed system may be that the opening, the observation window, and the fluid curtain nozzle are disposed substantially in alignment with one another on the distal end surface.

As described above, bubbles generated at the opening are securely kept away from the observation window by a fluid curtain formed by disposing the opening, the observation window and the fluid curtain nozzle substantially in alignment with one another. Thus, it is possible to secure the visual field of the observation window.

Yet additionally, as shown in a third aspect of the present invention, the endoscope gas feed system may be that the width of the fluid curtain nozzle is larger than the maximum diameter of the opening for spraying the constant-pressure feed gas.

Consequently, bubbles generated near the constant-pressure feed gas spray port can be securely moved away from the observation window by a fluid curtain.

Still additionally, as shown in a fourth aspect of the present invention, the endoscope gas feed system may be that the opening is a forceps port, a constant-pressure gas feed conduit for supplying the constant-pressure feed gas to the opening is a forceps channel formed within the insertion part of an endoscope, and the constant-pressure gas feed unit supplies the constant-pressure feed gas through the forceps channel.

Still additionally, as shown in a fifth aspect of the present invention, the endoscope gas feed system may be that the opening is a feed gas spray port provided on the distal end surface separately from the forceps port, the constant-pressure gas feed conduit for supplying the constant-pressure feed gas to the opening is a gas feed channel formed within the insertion part of the endoscope, and the constant-pressure gas feed unit supplies the constant-pressure feed gas through the gas feed channel.

As described above, the gas feed conduit for supplying the constant-pressure feed gas to the distal end surface of an endoscope is not limited in particular, but the present invention is applicable to various types of gas feed conduits.

Still additionally, as shown in a sixth aspect of the present invention, the endoscope gas feed system may be that the fluid curtain-forming gas feed unit continuously supplies a gas to the fluid curtain nozzle all the while the constant-pressure gas feed unit is engaged in constant-pressure gas supply.

Consequently, the visual field of the observation window being used for observation can be prevented from being interrupted by bubbles, and wasteful gas supply can be suppressed by forming a fluid curtain only while pneumoperitoneum is applied to within a lumen and endoscopic observations and treatments are performed.

Still additionally, as shown in a seventh aspect of the present invention, the endoscope gas feed system may be that both of the gasses supplied by the constant-pressure gas feed unit and the fluid curtain-forming gas feed unit are a carbon dioxide gas.

By using a carbon dioxide gas used for pneumoperitoneum also for a fluid curtain, as described above, it is possible to simplify the configuration of the gas feed unit.

Still additionally, as shown in an eighth aspect of the present invention, the endoscope gas feed system may be that the constant-pressure gas feed unit and the fluid curtain-forming gas feed unit are configured with one gas feed unit.

Consequently, it is possible to simplify the configuration of apparatus and reduce the cost thereof.

Also in order to achieve the above-described object, a ninth aspect of the present invention provides an endoscope comprising: an observation window disposed on a distal end surface of the insertion part of the endoscope, an opening for spraying a constant-pressure feed gas disposed on a distal end surface of the insertion part of the endoscope, and a fluid curtain nozzle disposed on a distal end surface of the insertion part of the endoscope, said fluid curtain nozzle blowing a fluid curtain-forming gas toward the observation window and being disposed on an opposite side of the opening with respect to the observation window, so that the fluid curtain nozzle, the observation window and the opening are substantially in alignment with one another.

Consequently, even if bubbles are generated by a gas sprayed from the opening for spraying the constant-pressure feed gas, the bubbles are moved to a side opposite to the observation window by a fluid curtain. Accordingly, when a constant-pressure gas supply is provided through the opening formed on the distal end surface of the endoscope, the visual field of the observation window can be prevented from being interrupted by bubbles generated near a gas spray port, thereby securing the visual field of the observation window.

Also in order to achieve the above-described object, a tenth aspect of the present invention provides an endoscope system comprising an endoscope gas feed system according to any one of the first to eighth aspects and an endoscope according to the ninth aspect.

Consequently, even if bubbles are generated by a gas sprayed from the opening for spraying the constant-pressure feed gas, the bubbles are moved to a side opposite to the observation window by a fluid curtain. Accordingly, when a constant-pressure gas supply is provided through the opening formed on the distal end surface of the endoscope, the visual field of the observation window can be prevented from being interrupted by bubbles generated near a gas spray port, thereby securing the visual field of the observation window.

As has been described heretofore, according to the present invention, even if bubbles are generated by a gas sprayed from the opening for spraying the constant-pressure feed gas, the bubbles are moved to a side opposite to the observation window by a fluid curtain. Accordingly, when a constant-pressure gas supply is provided through the opening formed on the distal end surface of the endoscope, the visual field of the observation window can be prevented from being interrupted by bubbles generated near a gas spray port, thereby securing the visual field of the observation window.

DETAILED DESCRIPTION OF THE PREFERRED EMBODIMENTS

Hereinafter, an endoscope gas feed system, an endoscope and an endoscope system according to the present invention will be described in detail with reference to the accompanying drawings.

Figure 1:
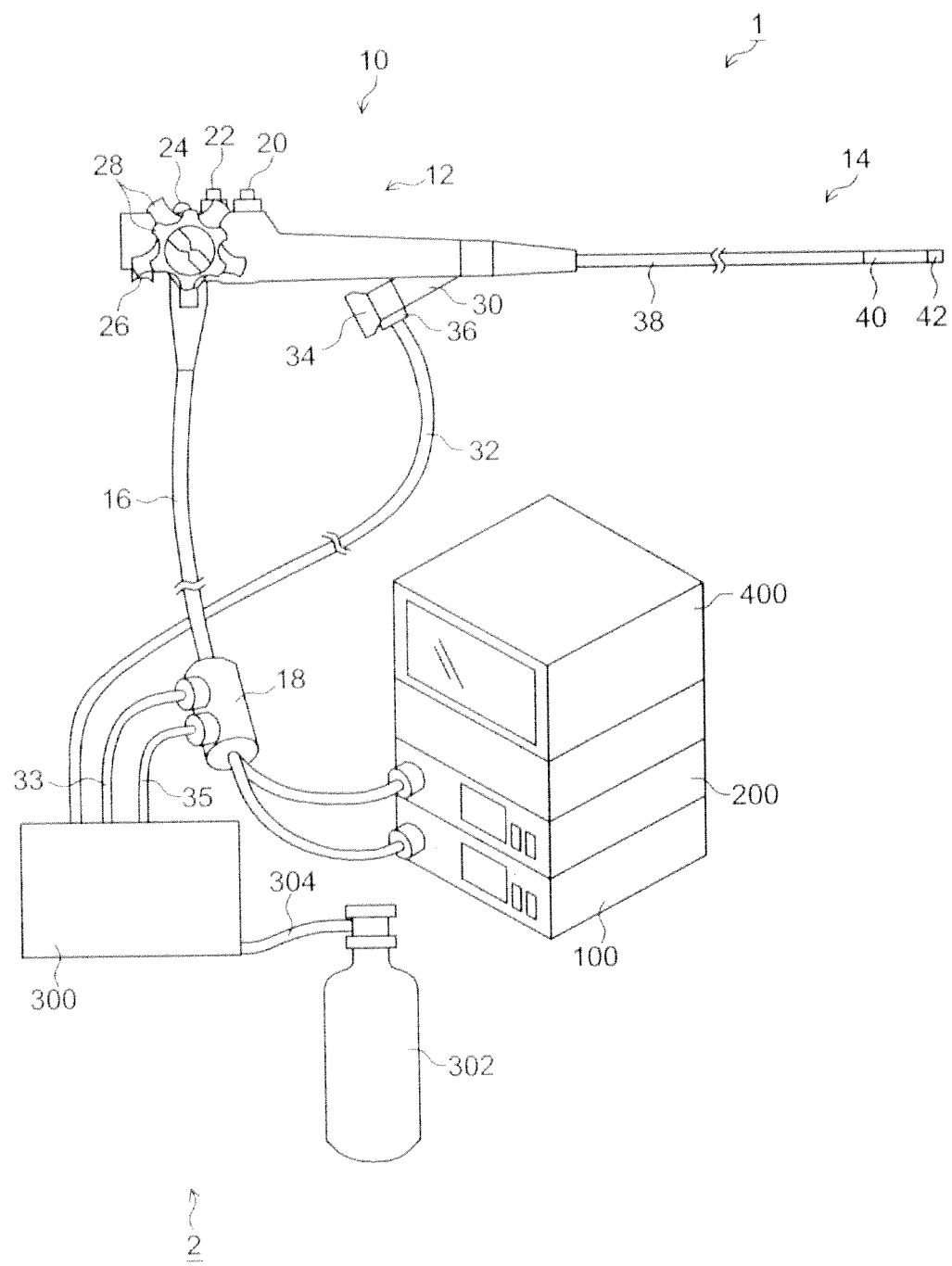
FIG. 1 is an external view illustrating the schematic overall configuration of a first embodiment of an endoscope system equipped with an endoscope gas feed system according to the present invention.

FIG. 1 is an external view illustrating the schematic overall configuration of a first embodiment of an endoscope system equipped with an endoscope gas feed system according to the present invention.

As illustrated in FIG. 1, an endoscope system 1 is equipped with an endoscope gas feed system 2. The endoscope system 1 is comprised mainly of an endoscope (flexible endoscope) 10, the endoscope gas feed system 2, a light source unit 100, an endoscope processor 200, and a monitor unit 400.

The endoscope 10 includes a hand-operated part 12 and an insertion part 14 connected continuously to this hand-operated part 12. An operator holds the hand-operated part 12 located on the proximal end side of the endoscope 10 to operate the endoscope 10 and, by inserting the distal end side of the insertion part 14 into a lumen of a subject being tested, performs observations, diagnoses or curative treatments.

A universal cable 16 is connected to the hand-operated part 12, and an endoscope connector 18 is provided on the universal cable 16. By attachably and detachably coupling this endoscope connector 18 with the light source unit 100, illuminating light is sent to an illuminating optical system (not illustrated) disposed at the distal end portion of the insertion part 14. In addition, an electrical connector is connected to the endoscope connector 18 through the universal cable 16, and the electrical connector is attachably and detachably coupled with the endoscope processor 200. Consequently, observed image data obtained with the endoscope 10 is output to the endoscope processor 200, so that an observed image is displayed on the monitor unit 400 connected to the endoscope processor 200.

In addition, the hand-operated part 12 is provided with a gas/water feed button 20, a suction button 22, a shutter button 24, a seesaw switch 26 for zooming operation, angle knobs 28, and a forceps insertion part 30.

The forceps insertion part 30 is communicated with an unillustrated forceps channel formed within the insertion part 14. As will be described later, the forceps channel is communicated with a forceps port (see FIG. 2) of the distal end portion of the endoscope.

When a carbon dioxide gas is supplied into a lumen as the constant-pressure feed gas through the forceps channel, an insertion inlet adapter 34 is provided on the forceps insertion part 30. A constant-pressure gas feed tube (gas feed tube) 32 is coupled with a gas supply cap 36 of the insertion inlet adapter 34. In addition, the other end of the gas feed tube 32 is coupled with a gas feed unit 300.

A carbon dioxide gas cylinder 302 is coupled with the gas feed unit 300 through a high-pressure gas tube 304. A carbon dioxide gas is stored in a liquefied state in the carbon dioxide gas cylinder 302.

The carbon dioxide gas stored in the carbon dioxide gas cylinder 302 is introduced from the forceps insertion part 30 to the forceps channel through the gas feed tube 32 by the gas feed unit 300 as a constant-pressure gas regulated to a predetermined pressure, so that the carbon dioxide gas is sprayed into a lumen of a subject being tested from the forceps port of the distal end portion of the endoscope.

In addition, a gas feed tube 33 for supplying a fluid curtain (gas curtain)-forming gas to be described later and a gas/water feed tube 35 for supplying a gas for cleaning the observation window (described later; see FIG. 2) are connected from the gas feed unit 300 to the endoscope connector 18. Note that although the gas feed tube 33 and the gas/water feed tube 35 are provided as separate members here, these tubes may be integrated into one tube.

The gas feed tube 33 is communicated with a gas feed channel (not illustrated) formed within the insertion part 14 through the conduit of the universal cable 16. As will be described later (see FIG. 2), the gas feed channel is connected to a fluid curtain nozzle formed on the distal end surface of a distal end portion 42, so as to blow a gas supplied from the gas feed unit 300 through the gas feed tube 33 out of the fluid curtain nozzle, thereby forming a fluid curtain (gas curtain) on the distal end surface.

The gas/water feed tube 35 is also communicated with a gas/water feed channel formed within the insertion part 14 through the conduit of the universal cable 16. The gas/water feed channel is connected to a gas/water feed nozzle formed on the distal end surface of the distal end portion 42. A gas supplied to the gas/water feed tube 35 by the gas feed unit 300 is sprayed from the gas/water feed nozzle of the distal end surface of the distal end portion 42 toward the observation window. Note that the gas/water feed nozzle may be integrated with the fluid curtain nozzle, and a gas may be supplied from one tube provided by integrating the gas feed tube 33 and the gas/water feed tube 35, as described above.

The insertion part 14 is composed of a flexible portion 38, a bending portion 40, and the distal end portion 42. The bending portion 40 is remotely bend-operated by rotating a pair of angle knobs 28 provided on the hand-operated part 12. Consequently, the distal end portion 42 can be directed in a desired direction. In addition, the flexible portion 38 connects between the hand-operated part 12 and the bending portion 40 and is made of a flexible member, so as to bend in an optional direction along a direction of insertion into an object being examined.

Figure 2:
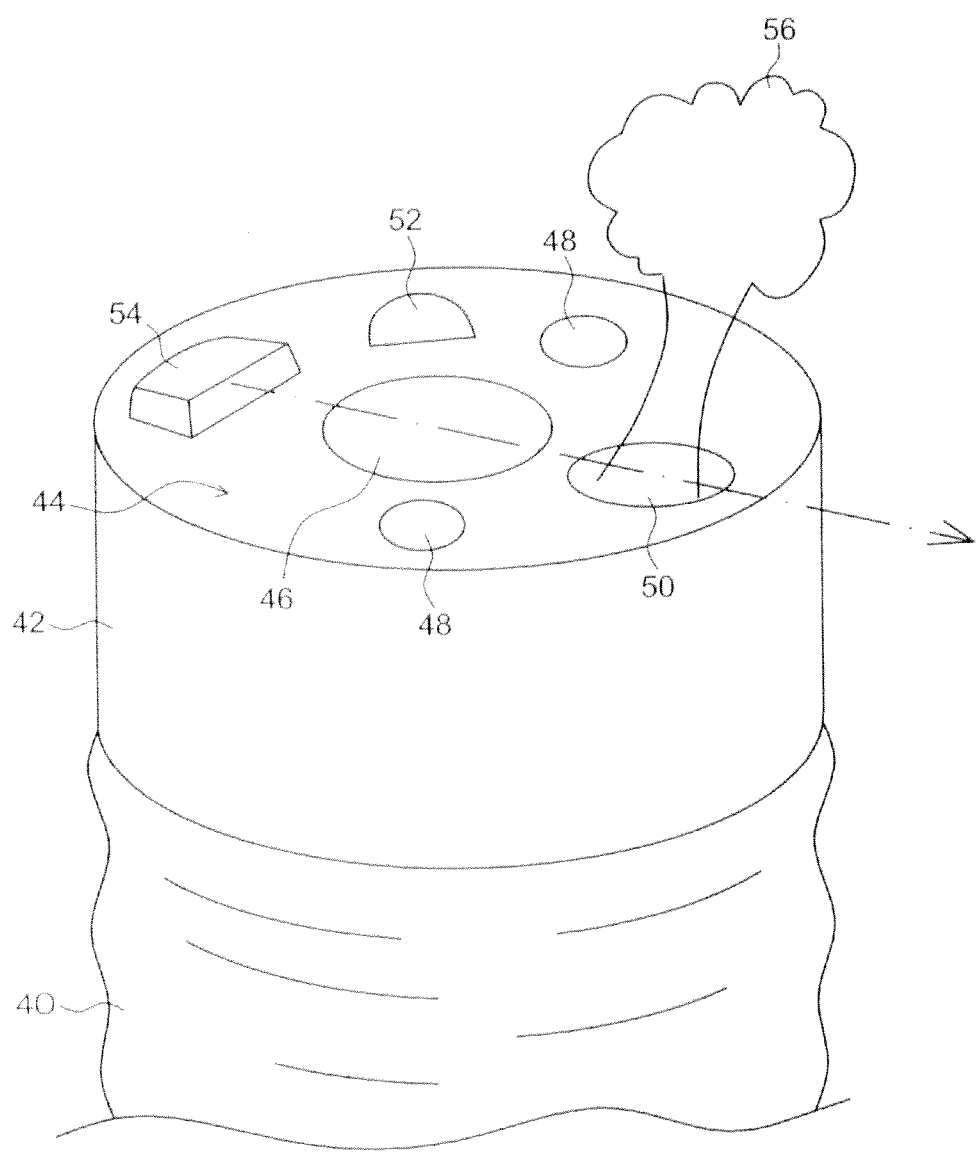
FIG. 2 is a perspective view illustrating a distal end portion of the insertion part of an endoscope of the first embodiment.

FIG. 2 perspectively illustrates the distal end portion 42 of the insertion part 14.

As illustrated in FIG. 2, the distal end portion 42 is provided at the leading end of the insertion part 14 in continuous connection with the bending portion 40. An observation window 46, an illumination window 48, a forceps port 50, a gas/water feed nozzle 52, and a fluid curtain nozzle 54 for spraying a fluid curtain (gas curtain)-forming gas are provided on a distal end surface 44 of the distal end portion 42.

An optical system (observation optical system) for capturing image light within an object being examined is disposed at the back of the observation window 46. The captured image light representative of an observed image is received by a CCD and sent to the endoscope processor 200 through a signal cable. The image light is then converted into a video signal at the endoscope processor 200, so that the observed image is displayed on the monitor unit 400 connected to the endoscope processor 200.

Two illumination windows 48 are disposed in symmetrical positions on both sides of the observation window 46, as illustrated in FIG. 2. Illuminating light from the light source unit 100 is irradiated through the illumination windows at an observed site within the object being examined. Light from the light source unit 100 is guided to the illumination windows 48 by an optical fiber (light guide) located within the insertion part 14. Thus, illuminating light is emitted through an illumination lens disposed at a leading end of the optical fiber and a cover glass fitted in each illumination window 48.

The forceps port 50 is connected to a forceps channel (not illustrated) disposed within the insertion part 14 and communicated with the forceps insertion part 30 of the hand-operated part 12. A leading end of each of forceps and various other treatment instruments inserted into the forceps insertion part 30 is exposed out of the forceps port 50 through the forceps channel.

In the present embodiment in particular, a carbon dioxide gas is supplied as the constant-pressure feed gas from the forceps port 50 into a lumen through the forceps channel. When the carbon dioxide gas is supplied into the lumen, the insertion inlet adapter 34 is mounted on the forceps insertion part 30, so that the carbon dioxide gas is supplied into the lumen from the gas supply cap 36 of the insertion inlet adapter 34 through the gas feed tube 32 coupled with the gas feed unit 300.

The gas/water feed nozzle 52 is used to clean the observation window 46 by spraying a cleaning fluid and pressurized air when the observation window 46 becomes contaminated. The gas/water feed nozzle 52 sprays fluids, such as pressurized air and cleaning water, toward the observation window 46 in response to gas feed operation and water feed operation performed by using the gas/water feed button 20 provided on the hand-operated part 12. Consequently, bodily fluids and feculence attached to the observation window 46 are cleaned off and thus an excellent visual field is secured.

Note that a carbon dioxide gas supplied from the gas feed unit 300 is suitably used as the pressurized air sprayed from the gas/water feed nozzle 52.

When a carbon dioxide gas is supplied from the forceps port 50 into a lumen, however, bubbles may be generated due to bodily fluids and water attached to the distal end surface 44. Consequently, the generated bubbles may, for example, cover the observation window 46, thus interrupting the visual field thereof. As a result, the observation window 46 has to be cleaned frequently using the gas/water feed nozzle 52.

Hence, in the present embodiment, a fluid curtain is formed on the distal end surface 44, so that even if bubbles are generated from the carbon dioxide gas sprayed out of the forceps port 50 and from liquids attached to the distal end surface 44, the bubbles do not go into the visual field area of the observation window 46, thereby securing the visual field thereof.

That is, as illustrated in FIG. 2, the fluid curtain nozzle 54 for spraying a fluid curtain (gas curtain)-forming gas is provided on the distal end surface 44.

A gas (carbon dioxide gas) is supplied, by way of the gas feed channel within the insertion part 14, from the gas feed unit 300 to the fluid curtain nozzle 54 through the gas feed tube 32, the endoscope connector 18, and the conduit of the universal cable 16.

In order to blow off bubbles generated at the forceps port 50 to a side opposite to the observation window 46 by a fluid curtain, the fluid curtain nozzle 54 is located on the opposite side of the forceps port 50 with respect to the observation window 46.

In particular, the fluid curtain nozzle 54 is disposed so as to be substantially in alignment with the observation window 46 and the forceps port 50. In addition, the gas blowout direction of the fluid curtain nozzle 54 is pointed to the observation window 46.

Accordingly, a fluid curtain that flows so as to run over the observation window 46 and then the forceps port 50, as shown by an arrowed chain line in the figure, is formed by constantly blowing a gas (carbon dioxide gas) from the fluid curtain nozzle 54.

Consequently, a constant-pressure feed gas (carbon dioxide gas) 56 sprayed from the forceps port 50 is blown off in the opposite direction of the observation window 46 by this fluid curtain. Thus, the gas does not go into the visual field area of the observation window 46.

As a result, even if bubbles are generated by a gas sprayed from the forceps port 50, the generated bubbles are prevented from expanding toward the observation window 46 and attaching thereto, thus interrupting the visual field of the observation window 46.

Note that in order to move bubbles away from the observation window 46 by a fluid curtain, the width of the fluid curtain nozzle 54 is made larger than the diameter (maximum diameter) of the forceps port 50 for spraying a constant-pressure feed gas, so that the fluid curtain is formed so as to be larger in width than at least the diameter (maximum diameter) of the forceps port 50.

Even if bubbles generated at the forceps port 50 is blown off by a fluid curtain, the bubbles may spread peripherally. In order to more reliably secure the visual field of the observation window 46 by keeping bubbles away therefrom, the width of the fluid curtain nozzle 54 is preferably made larger than the maximum diameter of the observation window 46, so that the width of the fluid curtain is larger than the maximum diameter of the observation window 46.

Next, a second embodiment of the present invention will be described.

In the first embodiment shown above, a constant-pressure feed gas is sprayed from the forceps port 50 into a lumen. In the second embodiment, however, a constant-pressure gas feed channel is provided within the insertion part 14 and a constant-pressure feed gas spray port is formed on the distal end surface 44, so that a gas supplied from the constant-pressure gas feed channel is sprayed from the constant-pressure feed gas spray port, rather than from the forceps port 50. In addition, this constant-pressure feed gas spray port is disposed so as to be substantially in alignment with the fluid curtain nozzle 54 and the observation window 46.

Figure 3:
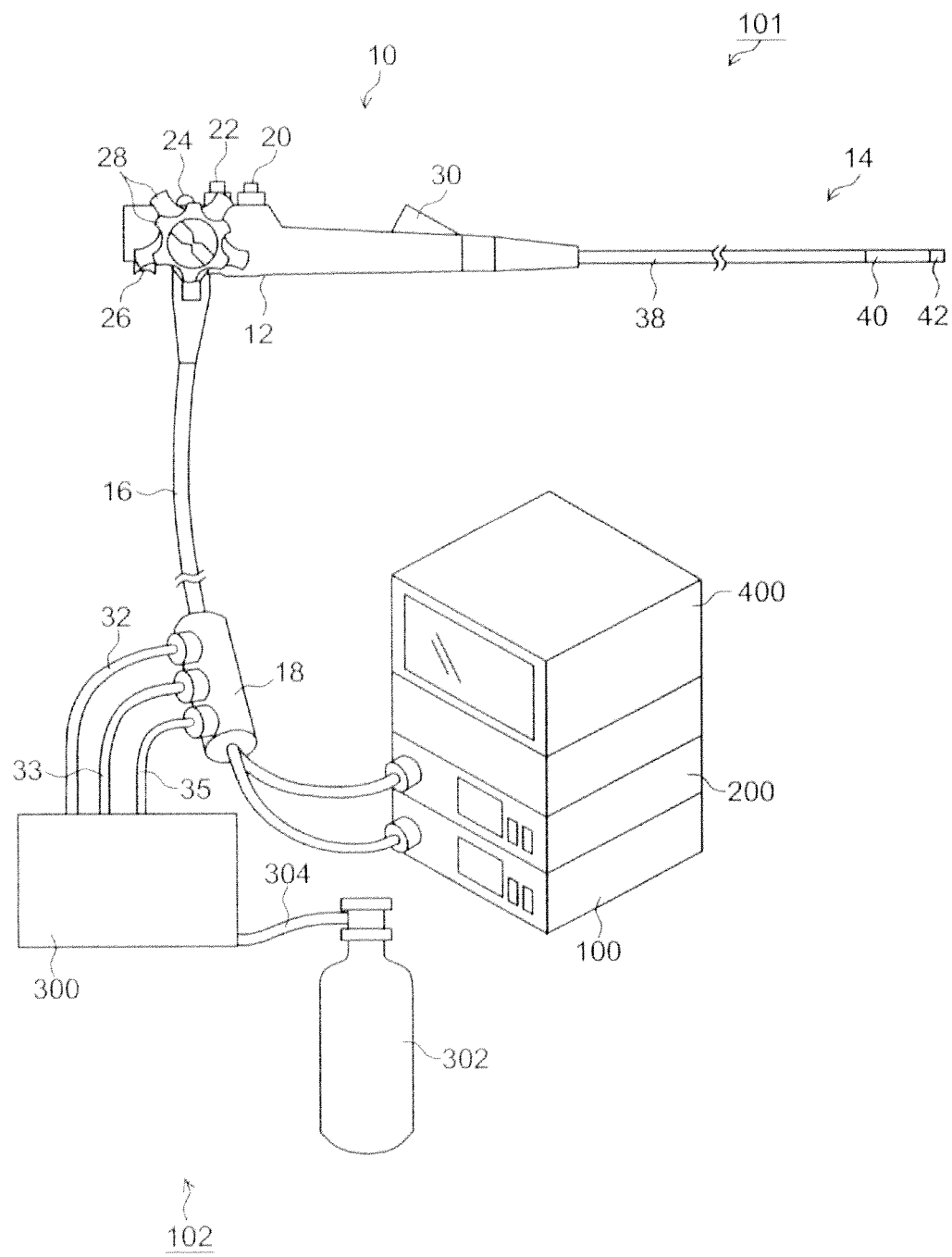
FIG. 3 is an external view illustrating the schematic overall configuration of a second embodiment of an endoscope system equipped with an endoscope gas feed system according to the present invention.

FIG. 3 illustrates the schematic overall configuration of a second embodiment of an endoscope system equipped with an endoscope gas feed system according to the present invention.

As illustrated in FIG. 3, an endoscope system 101 of the present embodiment is equipped with an endoscope gas feed system 102.

In the endoscope gas feed system 102 of the present embodiment, a constant-pressure feed gas is not sprayed from the forceps port of the distal end surface into a lumen of a subject being tested. Instead, the gas is sprayed from a spray port of the distal end surface through a gas feed channel formed within the insertion part 14, as will be described in detail later (see FIG. 4).

Accordingly, the gas feed tube 32 for supplying the constant-pressure feed gas from the gas feed unit 300 is connected to a gas feed conduit within the universal cable 16 through the endoscope connector 18, rather than to the forceps insertion part 30 as in the first embodiment.

Note that since the rest of the configuration of the present embodiment is all the same as that of the above-described first embodiment, respective constituent elements are assigned with the same reference numerals as those of the first embodiment shown in FIG. 1 and will be described in no further detail.

Figure 4:
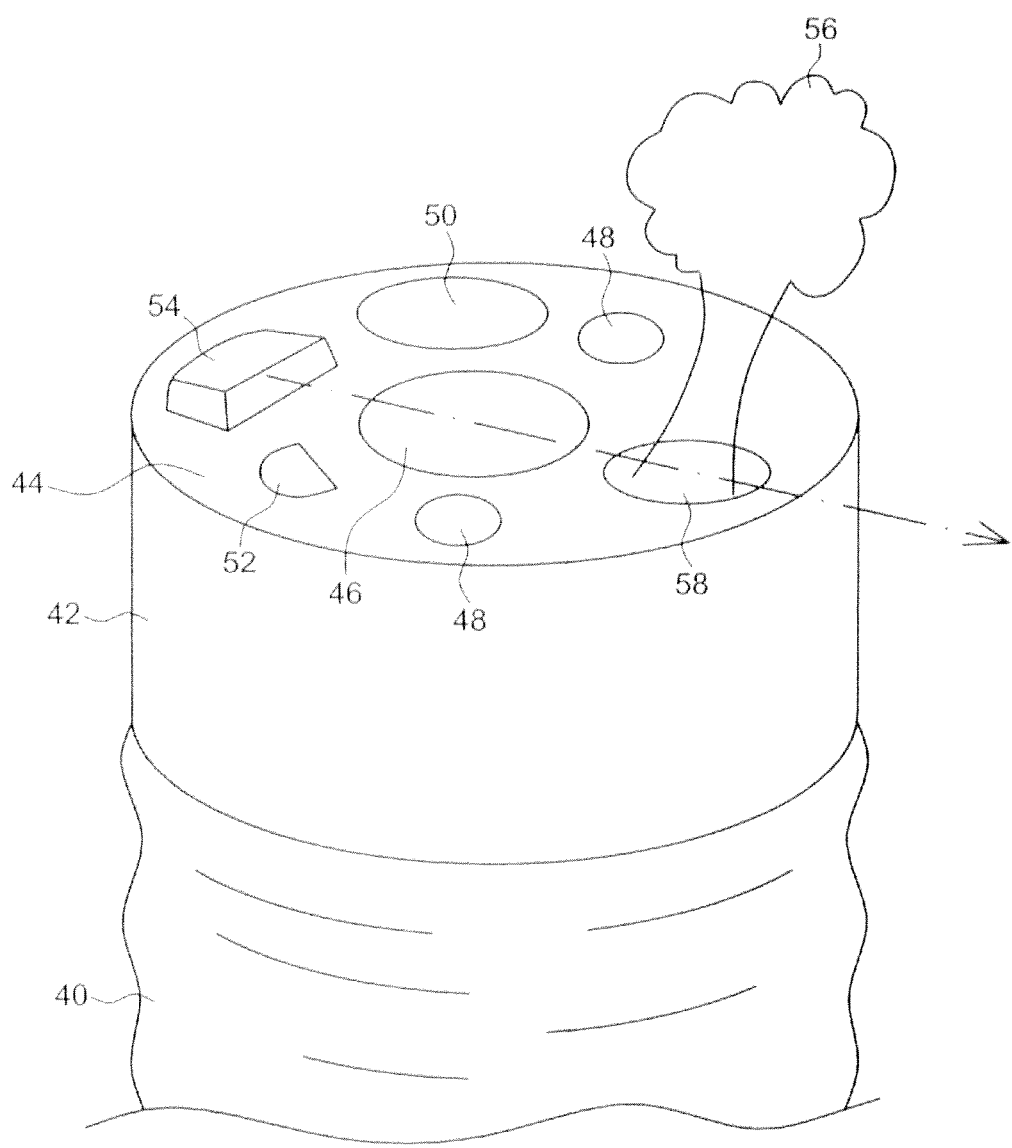
FIG. 4 is a perspective view illustrating a distal end portion of the insertion part of an endoscope of the second embodiment.

FIG. 4 perspectively illustrates the distal end portion 42 of the insertion part 14.

As illustrated in FIG. 4, an observation window 46, an illumination window 48, a forceps port 50, a gas/water feed nozzle 52, a fluid curtain nozzle 54 for spraying a fluid curtain (gas curtain)-forming gas, and a constant-pressure feed gas spray port 58 are provided on the distal end surface 44 of the distal end portion 42.

The forceps port 50 is connected to a forceps channel (not illustrated) disposed within the insertion part 14 and communicated with the forceps insertion part 30 of the hand-operated part 12. A leading end of each of forceps and various other treatment instruments inserted into the forceps insertion part 30 is exposed out of the forceps port 50 through the forceps channel.

The constant-pressure feed gas spray port 58 is communicated with a gas feed channel provided within the insertion part 14. A constant-pressure feed gas (carbon dioxide gas) is supplied to the gas feed channel from the gas feed unit 300 through the gas feed tube 32 and a gas feed conduit within the universal cable 16. Consequently, a constant-pressure feed gas 56 is sprayed from the constant-pressure feed gas spray port 58 into a lumen of a subject being tested.

In the present embodiment, as illustrated in FIG. 4, the fluid curtain nozzle 54 is formed on the opposite side of the constant-pressure feed gas spray port 58 with respect to the observation window 46.

In particular, the fluid curtain nozzle 54 is disposed so as to be substantially in alignment with the observation window 46 and the constant-pressure feed gas spray port 58 on the distal end surface 44, and to spray a fluid curtain gas toward the observation window 46.

A fluid curtain is formed by a gas flow in a direction shown by a chain line on the distal end surface in the figure caused by a gas (carbon dioxide gas the same as the constant-pressure feed gas) blown from the fluid curtain nozzle 54.

Consequently, even if bubbles are generated by the constant-pressure feed gas 56 sprayed from the constant-pressure feed gas spray port 58, the bubbles are moved by a fluid curtain in a direction away from the observation window 46. Thus, the visual field of the observation window 46 is not interrupted by the bubbles, and therefore, can be secured.

Having thus described two embodiments hereinabove, it is possible, in either embodiment, to prevent bubbles generated by the constant-pressure feed gas from interrupting the visual field of the observation window 46, by disposing the fluid curtain nozzle 54, the observation window 46 and an opening for spraying a constant-pressure feed gas so as to be in alignment with one another and blowing a gas from the fluid curtain nozzle 54 to constantly form a regular flow of gas on the distal end surface 44.

While an endoscope gas feed system, an endoscope and an endoscope system according to the present invention have been described in detail hereinabove, the present invention is not limited to the above-described embodiments. It is needless to say that various modifications and alterations may be made to the present invention without departing from the gist thereof.

What is claimed is:

1. An endoscope gas feed system, comprising:
    an insertion part of an endoscope configured for insertion into a body cavity and having a distal end surface, the distal end surface including:
        an observation window; and
        an opening for spraying a constant-pressure feed gas,
        a fluid curtain nozzle for blowing a fluid curtain-forming gas toward the observation window provided on the distal end surface of the insertion part of the endoscope, the fluid curtain nozzle is provided on an opposite side of the opening with respect to the observation window;
        a gas/water feed nozzle for cleaning the observation window, the gas/water feed nozzle being provided on the distal end surface;
    a constant-pressure gas feed unit for supplying the constant-pressure feed gas, so as to spray the constant-pressure feed gas from the opening; and
    a fluid curtain-forming gas feed unit for supplying a gas, so as to blow the fluid curtain-forming gas from the fluid curtain nozzle,
    wherein the opening, the observation window, and the fluid curtain nozzle are disposed substantially in alignment with one another on the distal end surface.

2. The endoscope gas feed system according to claim 1, wherein a width of the fluid curtain nozzle is larger than a maximum diameter of the opening for spraying the constant-pressure feed gas.

3. The endoscope gas feed system according to claim 1, wherein the opening comprises a forceps port, a constant-pressure gas feed conduit for supplying the constant-pressure feed gas to the opening comprises a forceps channel formed within the insertion part of an endoscope, and the constant-pressure gas feed unit supplies the constant-pressure feed gas through the forceps channel.

4. The endoscope gas feed system according to claim 1, wherein the opening comprises a feed gas spray port provided on the distal end surface separately from a forceps port, a constant-pressure gas feed conduit for supplying the constant-pressure feed gas to the opening comprises a gas feed channel formed within the insertion part of the endoscope, and the constant-pressure gas feed unit supplies the constant-pressure feed gas through the gas feed channel.

5. The endoscope gas feed system according to claim 1, wherein the fluid curtain-forming gas feed unit continuously supplies a gas to the fluid curtain nozzle all the while the constant-pressure gas feed unit is engaged in constant-pressure gas supply.

6. The endoscope gas feed system according to claim 1, wherein both of the gasses supplied by the constant-pressure gas feed unit and the fluid curtain-forming gas feed unit comprise a carbon dioxide gas.

7. The endoscope gas feed system according to claim 6, wherein the constant-pressure gas feed unit and the fluid curtain-forming gas feed unit are configured with one gas feed unit.

8. An endoscope comprising:
    an insertion portion of the endoscope, the insertion portion having a distal end surface;
    an observation window disposed on the distal end surface of the insertion part of the endoscope,
    a gas/water feed nozzle for cleaning the observation window, the gas/water feed nozzle being provided on the distal end surface;
    an opening for spraying a constant-pressure feed gas disposed on a distal end surface of the insertion part of the endoscope, and
    a fluid curtain nozzle disposed on a distal end surface of the insertion part of the endoscope, said fluid curtain nozzle blowing a fluid curtain-forming gas toward the observation window and being disposed on an opposite side of the opening with respect to the observation window, so that the fluid curtain nozzle, the observation window, and the opening are substantially in alignment with one another.

9. An endoscope system comprising an endoscope gas feed system according to claim 1.

10. An endoscope system comprising an endoscope according to claim 8.

11. The endoscope gas feed system according to claim 1, wherein a blowout direction of the fluid curtain nozzle is pointed at the observation window.

12. The endoscope gas feed system according to claim 1, wherein a width of the fluid curtain nozzle is larger than a maximum diameter of the observation window.

13. The endoscope gas feed system according to claim 2, wherein a width of the fluid curtain nozzle is larger than a maximum diameter of the observation window.

14. The endoscope gas feed system according to claim 1, wherein the fluid curtain nozzle is configured to blow the fluid curtain-forming gas towards the constant-pressure feed gas sprayed from the opening.

15. The endoscope gas feed system according to claim 1, further comprising a gas/water feed unit for supplying a cleaning gas/fluid, so as to spray the cleaning gas/fluid from the gas/water feed nozzle.

16. The endoscope gas feed system according to claim 15, wherein the gasses supplied by the constant-pressure gas feed unit, the gas/water feed unit, and the fluid curtain-forming gas feed unit comprise a carbon dioxide gas.

17. The endoscope gas feed system according to claim 16, wherein the constant-pressure gas feed unit, the gas/water feed unit, and the fluid curtain-forming gas feed unit are configured as one gas feed unit.

18. The endoscope gas feed system according to claim 16, wherein the gas/water feed nozzle is configured to spray the carbon dioxide gas as pressurized air.

19. The endoscope gas feed system according to claim 8, further comprising a gas/water feed unit for supplying a cleaning gas/fluid, so as to spray the cleaning gas/fluid from the gas/water feed nozzle.

20. An endoscope gas feed system, comprising:
an insertion part of an endoscope configured for insertion into a body cavity and having a distal end surface, the distal end surface including:
an observation window; and
an opening for spraying a constant-pressure feed gas,
a fluid curtain nozzle for blowing a fluid curtain-forming gas toward the observation window provided on the distal end surface of the insertion part of the endoscope, the fluid curtain nozzle is provided on an opposite side of the opening with respect to the observation window;
a gas/water feed nozzle for cleaning the observation window, the gas/water feed nozzle being provided on the distal end surface;
a constant-pressure gas feed unit for supplying the constant-pressure feed gas, so as to spray the constant-pressure feed gas from the opening; and
a fluid curtain-forming gas feed unit for supplying a gas, so as to blow the fluid curtain-forming gas from the fluid curtain nozzle,
wherein a center of the fluid curtain nozzle, a center of the observation window, and a center of the opening fall inline.

* * * * *